United States Patent [19]

Park et al.

[11] Patent Number: 5,681,591
[45] Date of Patent: Oct. 28, 1997

[54] COMPOSITIONS AND METHODS FOR CONTACT LENS DISINFECTING

[75] Inventors: John Y. Park, Santa Ana; James N. Cook, Mission Viejo; Claude B. Anger, Long Beach, all of Calif.

[73] Assignee: Allergan, Waco, Tex.

[21] Appl. No.: 947,087

[22] Filed: Sep. 17, 1992

Related U.S. Application Data

[63] Continuation of Ser. No. 630,305, Dec. 19, 1990, abandoned.

[51] Int. Cl.$^6$ ............................................. A61K 33/40
[52] U.S. Cl. ......................................... 424/616; 514/912
[58] Field of Search ............................... 424/616; 514/912

[56] References Cited

U.S. PATENT DOCUMENTS

| Re. 32,672 | 5/1988 | Huth et al. | 252/95 |
|---|---|---|---|
| 3,065,139 | 11/1962 | Ericsson | 167/72 |
| 4,119,557 | 10/1978 | Postlethwaite | 252/99 |
| 4,311,598 | 1/1982 | Verachtert | 210/757 |
| 4,414,127 | 11/1983 | Fu . | |
| 4,473,550 | 9/1984 | Rosenbaum et al. | 424/94 |
| 4,476,108 | 10/1984 | Kessler et al. . | |
| 4,490,389 | 12/1984 | Nelson et al. . | |
| 4,568,477 | 2/1986 | Oakes | 252/99 |
| 4,588,586 | 5/1986 | Kessler et al. | 424/94 |
| 4,620,935 | 11/1986 | Baxter et al. | 252/94 |
| 4,631,141 | 12/1986 | Baxter | 252/99 |
| 4,728,455 | 3/1988 | Rerek | 252/99 |
| 4,757,014 | 7/1988 | Hendrickson et al. | 435/180 |

FOREIGN PATENT DOCUMENTS

| 0110609 | 6/1984 | European Pat. Off. . |
|---|---|---|
| 0142623 | 5/1985 | European Pat. Off. . |
| 142623 | 5/1985 | European Pat. Off. . |
| 0175801 | 4/1986 | European Pat. Off. . |
| 0458578 | 11/1991 | European Pat. Off. . |
| 2395034 | 1/1979 | France . |
| 2003033 | 3/1979 | United Kingdom . |
| WO8605695 | 10/1986 | WIPO . |

OTHER PUBLICATIONS

Robert R. Grinstead, Oxidation of Salicylate by the Model Peroxidase Catalyst Iron–Ethylenediaminetetraacetato–iron(III) Acid, Dec. 14, 1959, pp. 3472–3476.

Robert R. Grinstead, The Oxidation of Ascorbic Acid by Hydrogen Peroxide, Catalysis by Ethylenediaminetetraaceato–Iron(III), Dec. 14, 1959, pp. 3464–3471.

*Primary Examiner*—Zohreh Fay
*Attorney, Agent, or Firm*—Frank J. Uxa

[57] ABSTRACT

A composition useful for disinfecting a contact lens comprising a substantially isotonic, aqueous liquid medium containing hydrogen peroxide in an amount effective to disinfect a contact lens contacted with the aqueous liquid medium, and a hydrogen peroxide reducing agent dissolved in the aqueous liquid medium in an amount effective to enhance the antimicrobial activity of the aqueous liquid medium. Preferably, the composition further includes transition metal ions in an amount effective to further enhance the antimicrobial activity of the aqueous liquid medium and is substantially free of peroxidase.

17 Claims, No Drawings

5,681,591

COMPOSITIONS AND METHODS FOR CONTACT LENS DISINFECTING

This application is a continuation of application Ser. No. 630,305, filed Dec. 19, 1990 now abandoned.

BACKGROUND OF THE INVENTION

This invention relates to disinfecting lenses, such as contact lenses. In particular, the invention relates to compositions and methods useful to quickly and effectively disinfect lenses while reducing eye irritation caused by disinfecting the lenses.

Contact lenses should be periodically cleaned and disinfected by the user to prevent infection or other deleterious effects on ocular health which may be associated with contact lens wear. Currently, there are several different conventional systems and methods which enable the user to clean and disinfect their contact lenses between wearing times. These conventional cleaning and disinfection systems can be divided into "hot" and "cold" systems. Hot systems require the use of heat to disinfect the contact lenses, whereas cold systems use chemical disinfectants at ambient temperatures to disinfect the lenses.

Within the realm of cold disinfection systems are hydrogen peroxide disinfection systems. Disinfecting hydrogen peroxide solutions are effective to kill the bacteria and fungi which may contaminate contact lenses. However, residual hydrogen peroxide on a disinfected contact lens may cause irritation, burning or trauma to the eye unless this hydrogen peroxide is destroyed, i.e., decomposed, neutralized, inactivated or chemically reduced. Therefore, destruction of the residual hydrogen peroxide in the liquid medium containing the disinfected contact lens is needed to enable safe and comfortable wear of the disinfected contact lens. Liquid media (not including the hydrogen peroxide contained therein) used to disinfect contact lenses should be substantially isotonic and ophthalmically acceptable so as to reduce the chances of problems caused by placing the disinfected lenses in the wearer's eyes.

Aqueous hydrogen peroxide-containing solutions currently in use as contact lens disinfectants include relatively high concentrations of hydrogen peroxide, e.g., on the order of 3% (w/v). Such high hydrogen peroxide concentrations are used so that the contact lens can be disinfected in a reasonable period of time. Of course, the more residual hydrogen peroxide remaining after lens disinfecting, the more difficult and time consuming the problem of destroying this residual hydrogen peroxide. It would be advantageous to provide a contact lens disinfecting system in which reduced amounts of hydrogen peroxide can be employed.

Associated with the problem of hydrogen peroxide destruction in contact lens disinfection systems are the problems of easy use and user compliance. To enhance user compliance and ease of use, several efforts have focused on one-step disinfection and hydrogen peroxide destruction. In this regard, various time release tablets containing a core tablet including a hydrogen peroxide destroying component, and having a delayed release coating on the core tablet have been suggested.

International Patent Publication No. WO 86/05695 discloses a contact lens disinfecting agent which includes a hydrogen peroxide precursor, e.g., sodium percarbonate, a hydrogen peroxide inactivating agent, such as ene-diols and sulfurous acid derivatives, in delayed release form, and a color change indicator to indicate the inactivation of the disinfecting agent. The inactivating agent is provided in delayed release form so that after the composition has been added to water, and the contact lens has been added to the mixture, the disinfecting agent has sufficient time to disinfect the contact lens before release of the inactivating agent.

Rosenbaum et al U.S. Pat. No. 4,473,550 discloses sterilizing contact lenses using a combination of a peroxidase, hydrogen peroxide and a donor molecule, such as a phenylethylamine, benzoic acid, salicyclic acid and paraaminobenzoic acid. Kessler et al U.S. Pat. No. 4,588,586 discloses disinfecting contact lenses using a combination of a peroxidase, hydrogen peroxide and a source of donor molecules including ascorbic acid. This latter patent teaches that the donor molecules supply electrons which the peroxidase donates to hydrogen peroxide. Both patents teach that it is essential to employ a peroxidase as part of the disinfectant composition. It would be beneficial to provide contact lens disinfectant composition which has a reduced number of constituents, and/or does not rely on an intermediate enzymatic activation of hydrogen peroxide.

Nelson et al U.S. Pat. No. 4,490,389 discloses a method for a sterilizing hydrophilic (soft) contact lens by contacting such a lens with a composition having a pH between 6 and 9, and containing 0.01 to 0.03 weight percent of an ene-diol compound, such as ascorbic acid, and between 0.1 and 25 ppm copper ion in solution. The Nelson et al patent strongly implies that other disinfectants, such as hydrogen peroxide, which tend to accumulate on or in hydrophilic contact lens are not included in this composition. The system of Nelson et al is relatively slow in sterilizing or disinfecting contact lens, and is of little value in cleaning the lens, e.g., of protein-based debris.

Ericsson et al U.S. Pat. No. 3,065,139 discloses antiinfectant topical preparations which include a percarbonate, an ene-diol compound and ions of metals of atomic numbers 25 to 30, i.e., Cu, Fe, Mn, Ni, and Co. This patent does not disclose disinfecting contact lenses, the use of a buffer component to control pH or the use of any oxidizer other than percarbonate.

Verachtert U.S. Pat. No. 4,311,598 discloses treating municipal sewage or effluents from paper or food processing industries with a combination of hydrogen peroxide, a soluble copper salt and an autoxisable reducing agent, such as ascorbic acid or sodium sulphite. This patent does not disclose disinfecting contact lenses, any ophthalmic application, or the use of a buffer to control pH. For example, the Verachtert patent is not concerned with substantially isotonic solutions, which are important to use in ophthalmic applications, such as disinfecting contact lenses.

There continues to be a need for a contact lens care system which rapidly and effectively disinfects, and preferably cleans, a contact lens so that the disinfected lens can be safely and comfortably worn.

SUMMARY OF THE INVENTION

New compositions and methods useful for disinfecting, and preferably cleaning, a lens, in particular a contact lens, have been discovered. These compositions and methods take advantage of enhanced antimicrobial activity so that effective lens disinfecting can be achieved in relatively short time periods and/or using relatively reduced amounts of disinfectants, such as hydrogen peroxide. When reduced amounts of hydrogen peroxide are used, the amount of residual hydrogen peroxide that must be destroyed, e.g., to enable safe and comfortable wearing of the disinfected lens, is advantageously reduced. Further, the present system advantageously lends itself to a rapid and effective one step procedure for disinfecting, and preferably cleaning, a contact lens.

In one broad aspect, the present invention involves a composition useful for disinfecting a contact lens and which comprises an aqueous liquid medium, preferably a substantially isotonic aqueous liquid medium, containing hydrogen peroxide, and a hydrogen peroxide reducing agent, hereinafter referred to as a HPRA, present, e.g., dissolved, in the liquid medium in an activating amount effective to enhance the antimicrobial activity of the composition. The composition is substantially free of peroxidase in effective contact with hydrogen peroxide, in particular during the time hydrogen peroxide and HPRA together are acting to provide enhanced antimicrobial activity to disinfect the contact lens. In one embodiment, the composition further comprises a buffer component in an amount effective to maintain or control the pH of the composition as desired, in particular in the range of about 6 to about 8. The composition preferably has increased antimicrobial activity relative to a reference composition containing the same liquid medium and the same concentration of hydrogen peroxide as the composition and being substantially free of the HPRA. Preferably, the composition further includes transition metal ions, such as free and/or complexed transition metal ions, and/or halide ions and/or carbonate ions in an amount effective to further enhance the antimicrobial activity of the composition.

In another broad aspect, the present invention is directed to a composition which comprises hydrogen peroxide precursor and HPRA, e.g., as described above. Preferably one or both, more preferably both, of the hydrogen peroxide precursor and the HPRA are solid. In one embodiment, the hydrogen peroxide precursor is selected from such precursors other than percarbonate. The hydrogen peroxide precursor is capable of forming hydrogen peroxide in a liquid medium after being released in the liquid medium. The HPRA is present in an amount effective after being released, e.g., dissolved, in the liquid medium to enhance the antimicrobial activity of the composition/liquid medium combination. Preferably, this composition further includes transition metal ions and/or a transition metal ion source which forms transition metal ions in the liquid medium and/or halide ions and/or halide ion source which forms halide ions in the liquid medium and/or carbonate ions and/or a carbonate ion source which forms carbonate ions in the liquid medium. Such ions or ion sources are preferably present in an amount effective to further enhance the antimicrobial activity of the composition/liquid medium combination. The composition is preferably substantially free of peroxidase.

A further broad aspect involves a composition comprising hydrogen peroxide precursor capable of forming hydrogen peroxide in a liquid medium after being released in the liquid medium, HPRA, and hydrogen peroxide destroying component, hereinafter referred to as HPDC. Preferably at least one, and more preferably all three, of the hydrogen peroxide precursor, HPRA and HPDC are solid. The HPRA is present in an amount effective after being released in the liquid medium to enhance the antimicrobial activity of a composition comprising a hydrogen peroxide-containing liquid medium, hereinafter referred to as a HPLM. The HPDC is present in an amount effective after being released in the liquid medium to destroy substantially all the hydrogen peroxide present in the liquid medium. This composition is structured to release the HPRA in the liquid medium before the HPDC is so released, in particular at substantially the same time the hydrogen peroxide precursor is released in the liquid medium. This composition is substantially free of peroxidase which is to be released in the liquid medium prior to when the HPDC is so released. In one embodiment, the HPDC is a peroxidase and/or catalase, preferably catalase.

Methods of disinfecting contact lenses employing these compositions provide substantial benefits, e.g., rapid and effective lens disinfecting with little or no risk of eye irritation or discomfort as a result of wearing such disinfected lens.

DETAILED DESCRIPTION OF THE INVENTION

The present invention is of value where hydrogen peroxide is used to disinfect all types of lenses, e.g., contact lenses, which are benefited by periodical disinfecting. Such lenses, e.g., conventional contact lenses, in particular soft contact lenses, may be made of any suitable material or combination of materials and may have any suitable configuration not substantially deleteriously affected by hydrogen peroxide, the present compositions or the present methods.

The present invention takes advantage of the discovery that the combination of hydrogen peroxide and one or more of certain HPRAs, without requiring the presence of peroxidase, exhibit enhanced antimicrobial activity in contact lens disinfecting/cleaning applications without any substantial adverse effects on either the lens or the lens wearer. This is indeed surprising in view of the prior art, in particular Rosenbaum et al U.S. Pat. No. 4,473,550 and Kessler et al U.S. Pat. No. 4,588,586, which disclose peroxidase as an essential component in contact lens disinfecting compositions including peroxidase, hydrogen peroxide and donor molecules, such as ascorbic acid. This enhanced activity, which is preferably increased relative to the antimicrobial activity of a composition containing the same concentration of hydrogen peroxide and no HPRA, allows one to disinfect contact lens more rapidly and/or with less hydrogen peroxide. In any event, this combination provides substantial and unexpected benefits, particularly when one considers that a HPRA by definition chemically reduces or destroys hydrogen peroxide.

In one embodiment, the present invention involves a composition useful for disinfecting a lens, in particular a contact lens, comprising an aqueous liquid medium, preferably a substantially isotonic aqueous liquid medium, containing hydrogen peroxide and HPRA, preferably dissolved in the liquid medium, in an activating amount effective to provide enhanced antimicrobial activity, e.g., to enhance the antimicrobial activity of the composition. The composition is substantially free of peroxidase in effective contact with hydrogen peroxide, in particular during the time hydrogen peroxide and HPRA together are acting to provide enhanced antimicrobial activity to disinfect the lens. After the lens has been disinfected, a peroxidase and/or catalase, preferably catalase, can be released in the liquid medium to destroy any residual hydrogen peroxide remaining. Preferably, such composition has increased antimicrobial activity relative to a reference composition containing the same liquid medium, the same concentration of hydrogen peroxide and being substantially free of the HPRA contained in the composition.

The present composition comprising an aqueous liquid medium, hydrogen peroxide and HPRA is preferably used in a disinfecting amount. A disinfecting amount preferably means such amount as will reduce the microbial burden by one log in three hours. More preferably, the amount of such composition used is such that the microbial load is reduced by one log order in one hour. Particularly preferred are those amounts which reduce the microbial load by one log unit in 10 minutes or less. Aqueous hydrogen peroxide solutions, preferably containing about 0.5% to about 6% of hydrogen peroxide (w/v), are known to be effective disinfecting solutions for contact lenses. These solutions are effective at killing bacteria and fungi which may be found on contact lenses. In the present invention, because of the inclusion of an activating amount of HPRA, less hydrogen peroxide is often needed to effectively disinfect a contact lens in a reasonable or acceptable period of time. Thus, with less hydrogen peroxide present, less residual hydrogen peroxide needs to be destroyed so that the lens may be safely and comfortably worn on or in the eye. If this residual hydrogen peroxide is not destroyed before the lens is worn, irritation to the eye or wearing discomfort may occur. Thus, it is advantageous to use less hydrogen peroxide since this reduces the problem of destroying the residual hydrogen peroxide.

The presently useful HPRAs are present in amounts effective to provide enhanced antimicrobial activity. Care must be exercised in selecting the HPRA or HPRAs, and also in controlling the amount of HPRA or HPRAs used. In one embodiment, a relatively weak HPRA and/or a relatively small amount of HPRA is selected. The activating HPRA may be present in an amount less than that required to reduce all the hydrogen peroxide in the HPLM, in particular less than that required to reduce all the hydrogen peroxide in the HPLM at 70° F. within 5 hours after the HPRA is released into the HPLM. It is preferred to use a different HPDC, other than the HPRA being employed to enhance antimicrobial activity, to destroy the residual hydrogen peroxide remaining in the HPLM after the lens has been disinfected.

Any suitable HPRA may be employed provided it has no substantial detrimental effect on the present system, the lens being disinfected or on the wearer of the disinfected lens.

The HPRAs preferably have about the same or less, particularly less, hydrogen peroxide reducing activity than does glutathione. Glutathione itself is useful provided that the concentration of this HPRA is controlled. Other thiol components which have about the same or less hydrogen peroxide reducing activity than does glutathione are useful. Among such useful thiol components are cysteine, glutamyl cysteine, N-acetylcysteine, thiolactone, 2-oxo-thiazolidine-4-carboxylic acid and the like and mixtures thereof.

One particularly useful class of HPRA's are the ene-diol compounds. Examples of such compounds include ascorbic acid compounds, reductive acid compounds, isoascorbic acid compounds, glyoxylic acid compounds, squaric acid compounds, dihydroxymaleic acid compounds, dihydroxyfumaric acid compounds and mixtures thereof. Typical examples of the foregoing ene-diol compounds are the acids themselves, e.g., ascorbic acid, ophthalmically acceptable salts of such acids, e.g., sodium ascerbate, ophthalmically acceptable esters of such acids, e.g., ascorbyl palmitate and any other ophthalmically acceptable derivatives of such acids, e.g., that retain the ene-diol molecular structure. Mixtures of ene-diols may also be used. The preferred ene-diols are ascorbic acid, ophthalmically acceptable ascorbic acid salts, e.g., sodium or potassium, and mixtures thereof.

The amount of HPRA used varies depending, for example, on the specific HPRA being employed. In one embodiment, the amount of HPRA, and in particular the amount of ene-diol compound, may be less than that required to reduce all the hydrogen peroxide or potential hydrogen peroxide in the liquid medium in which the HPRA is employed, for example, in the range of about 0.01% to about 50% of that amount. However, the amount of HPRA employed is preferably at least equal to, and more preferably in excess of, that amount required to reduce all the hydrogen peroxide or potential hydrogen peroxide in the liquid medium in which the HPRA is employed. In this manner, the HPRA acts as a safety feature to prevent hydrogen peroxide in the liquid medium from inadvertently being placed in the lens wearer's eye with the disinfected lens. In one embodiment, the HPRA is included in a composition which is structured to release the HPRA in a liquid medium in two or more separate increments. For example, the composition can be structured to release an activating amount of HPRA in the liquid medium at substantially the same time the composition is introduced in the liquid medium. Then, after a period of time, in particular sufficient to effectively disinfect the lens, the remainder of HPRA is released in the liquid medium to destroy the residual hydrogen peroxide in the liquid medium.

In addition to the HPRA, the HPLM preferably further includes transition metal ions and/or halide ions and/or carbonate ions in an amount effective to further enhance the antimicrobial activity, e.g., of the composition. Thus, with such ions present, the lens disinfecting can be accomplished even faster and/or using even further reduced amounts of hydrogen peroxide.

Any suitable transition metal ions may be employed provided such ions have no substantial detrimental effect on the present system, the lens being disinfected or on the wearer of the disinfected lens. Such transition metals are selected from the metals of Groups IB, IIB, IIIB, VB, VIB, VIIB, and VIII of the Periodic Table of Elements. Examples of the transition metals the ions of which can be employed in the present invention include iron, manganese, chromium, vanadium, molybdenum, cobalt, nickel, copper, zinc, tungsten, the rare earth metals and mixtures thereof. Particularly useful transition metal ions are those of manganese, copper and mixtures thereof.

The transition metal ions useful in the present invention may be of any oxidation state or states. In a particularly useful embodiment, at least a portion of the HPRA is capable of forming a complex with the transition metal ions in the liquid medium. Care should be exercised in selecting the amount of transition metal ions to be included. Sufficient transition metal ions should be included to provide the desired enhancement in antimicrobial activity. However, large excesses should be avoided since metal-containing precipitates may form, and/or negative effects on the disinfected lens and/or the wearing of the disinfected lens may occur. The amount of transition metal ions included varies depending, for example, on the specific transition metal ions and HPRA being employed.

In one embodiment, the transition metal ions are preferably present in the liquid medium in an amount less than the amount, in moles, of the HPRA. If the transition metal ions are employed, such ions are preferably present in the liquid medium In an amount of at least about 1% and more preferably at least about 10%, based on moles, of the HPRA present in the liquid medium.

The transition metal ions are often derived from a precursor, e.g., solid precursor, which after release in, e.g., dissolution in, the liquid medium forms not only the transition metal cation, but also an anion. This anion should be chosen to be ophthalmically acceptable. Among the ophthalmically acceptable anions and useful transition metal salts useful as transition metal ion precursors are chloride ($Cl^-$), bromide, iodide, carbonate, sulfate, bisulfate, phosphate, acid phosphate, nitrate, acetate, maleate, fumarate, oxalate, lactate, tartrate, citrate, gluconate, saccharate, p-toluene sulfonate, and the like and mixtures thereof. The preferred ophthalmically acceptable anion is C⁻.

The use of cobalt ions and/or cobalt ion precursor, particularly in combination with the present HPRAs, has been found to provide a very effective indication of the presence of hydrogen peroxide in a liquid medium, particularly an aqueous liquid medium. With hydrogen peroxide present, the cobalt ion-containing liquid medium is green in color. However, with substantially no hydrogen peroxide present, e.g. after the hydrogen peroxide has been completely consumed or destroyed, the cobalt ion-containing liquid medium is pink in color.

The amount of cobalt ions and/or cobalt ion precursor used as a color indicator should be sufficient to provide the desired visual indication. This amount may be as little as about 1 ppm, preferably as little as about 5 ppm, by weight, based on the liquid medium being monitored, and calculated as elemental cobalt. Amounts of cobalt which provide for further enhanced antimicrobial activity in combination with the present HPRAs are generally useful to provide the color indication of the presence, or absence, of hydrogen peroxide.

The use of such a cobalt color indicator system provides substantial advantages. For example, the user of the present contact lens disinfection system can receive a visual indication that the residual hydrogen peroxide has been destroyed, and therefore, that the contact lens can be safely and comfortably worn.

Halide ions, in particular chloride ions, and/or carbonate ions provide for further enhancement of the antimicrobial activity in the present invention. Such anions can be included in the present compositions independently of the transition metal ions. For example, a saline solution may be used as the source of chloride ions. Also, ophthalmically acceptable metal halides and/or carbonates may be used as a precursor of such anions, e.g., in much the same way that the transition metal ion precursors are used to provide the presently useful transition metal ions. In one embodiment, transition metal halides and/or carbonates are employed so that the composition includes transition metal ions as well as halide ions and/or carbonate ions to enhance antimicrobial activity. The halide and/or carbonate ions are preferably present in the liquid medium at the same time the HPRA and hydrogen peroxide are present. If halide and/or carbonate ions are employed, such ions are preferably present in the liquid medium in an amount of at least about 1% and more preferably at least about 10%, based on moles, of the HPRA present in the liquid medium.

The liquid medium used is selected to have no substantial detrimental effect on the lens being treated and to allow, and preferably to even facilitate, the present lens treatment or treatments. The liquid medium is preferably aqueous-based. A particularly useful liquid aqueous medium is that derived from saline, e.g., a conventional saline solution. During the disinfecting contacting, it is preferred that the liquid aqueous medium have a pH in the range of about 3 to about 9, more preferably about 6 to about 8. The liquid medium, e.g., aqueous liquid medium, preferably includes a buffer component which is present in an amount effective to maintain the pH of the liquid medium in the desired range. This buffer component may be present in the liquid medium and/or may be introduced into the liquid medium, e.g., either separately or in combination with one or more of the other presently useful components, e.g., with the HPRA. Among the suitable buffer components or buffering agents which may be employed are those which are conventionally used in contact lens care products. Examples of useful buffer components include those with carbonate functionalities, bicarbonate functionalities, phosphate functionalities, borate functionalities, and the like and mixtures thereof. The buffers may be alkali metal and alkaline earth metal salts, in particular sodium and potassium.

In one embodiment, the HPRA or the combination of HPRA and transition metal ion precursor is included in a solid composition, e.g., a tablet, capsule, one or more solid particles and the like, which is preferably introduced into the HPLM about the same time as the lens to be disinfected is introduced into the HPLM. In addition, such solid compositions may further include a HPDC, preferably having a chemical make-up other than that of the HPRA, in an amount effective to destroy all the residual hydrogen peroxide remaining in the HPLM after the lens has been disinfected.

Thus, such solid compositions, which are preferably initially contacted with the HPLM at substantially the same time as is the lens to be disinfected, can provide for effective lens disinfection and, in addition, effectively destroy the residual hydrogen peroxide remaining in the HPLM so that the disinfected lens can be removed from the liquid medium and placed directly into the eye for safe and comfortable wear. Such solid compositions may be present in the form of at least one item, e.g., tablet, capsules, one or more solid particles and the like, which includes a coated portion, e.g., a core such as a core tablet, a barrier component and an outer portion. The coated portion or core includes the HPDC, which may be a further increment of the HPRA being employed or may be different from the HPRA being employed. The outer portion includes the HPRA, and preferably the transition metal ion precursor, and is released in the HPLM first, preferably very soon after the composition is initially contacted with the HPLM. The barrier component acts to delay the release of the HPDC from the coated portion in the HPLM for a period of time, preferably sufficient to allow the lens to be disinfected. Preferably, the barrier coating substantially surrounds the coated portion.

Any suitable HPDC may be included in the present compositions provided such HPDC has no substantial detrimental effect on the present system, on the disinfected lens or on the wearer of the disinfected lens. Among the useful HPDCs are strong hydrogen peroxide reducing agents, i.e., having greater hydrogen peroxide reducing activity than the HPRA used to provide enhanced antimicrobial activity, peroxidases, catalase, and mixtures thereof.

Examples of the strong hydrogen peroxide reducing agents which are useful in the present invention are alkali metal in particular sodium, thiosulfates; thiourea; alkali metal, in particular sodium, sulfites; thioglycerol; alkali metal, in particular sodium, formates; and the like and mixtures thereof. Particularly useful HPDC include peroxidases and catalase, preferably catalase. The peroxidases and catalase are very beneficial as the presently useful HPDC since such HPDCs are effective to substantially eliminate hydrogen peroxide from a liquid medium in a reasonable period of time, e.g., on the order of about 1 minute to about 12 hours, preferably about 5 minutes to about 1 hour, after the HPDC is initially released into the liquid medium.

The amount of HPDC employed is preferably sufficient to destroy all the hydrogen peroxide present in the HPLM into which the HPDC is placed. Excess HPDC may be employed. Very large excesses of HPDC are to be avoided since the HPDC itself may cause problems with the disinfected lens and/or the ability to safely and comfortably wear such disinfected lens. When catalase is employed as a HPDC, it is preferably present in an amount of about 100 to about 1000, more preferably about 150 to about 700 units of catalase activity per milliliter of liquid medium. For example, an especially useful amount of catalase for use in an aqueous solution containing about 3% (w/v) hydrogen peroxide is about 520 units of catalase activity/ml of solution.

The delayed release of the HPDC into the liquid medium may be accomplished in any one of many suitable ways, a number of which are conventional and well known in the art. For example, the barrier, component, e.g., coating, may be provided by coating a core tablet, or other particle, containing the HPDC with a slow dissolving coating material, which may ultimately be completely or only partially soluble in the liquid medium, or by including the HPDC in a matrix from which it may be slowly leached. Also, the matrix may be coated with a slow dissolving material so that the start of the slow release is delayed. The delayed release form of the HPDC is preferably such that substantially no release occurs during a delay period followed by rapid and substantially complete release of the HPDC at the end of the delay period. Such a result may be obtained by coating the HPDC with a slow dissolving coating.

Barrier components suitable as either coatings or as matrices, include water soluble vinyl polymers, such as polyvinylpyrrolidone, polyvinylalcohol and polyethyleneglycol; water soluble proteins; polysaccharide and cellulose derivatives, such as methyl cellulose, hydroxypropylmethyl cellulose, sodium carboxymethylcellulose; alginic acid and its salts and other derivatives; and the like and mixtures thereof. Mixtures of the above materials may be used.

The amount of barrier component used is not critical in the present invention provided that such barrier component functions as described herein. The barrier component or components may suitably be present in the range of about 1% to about 20% or more, based on the weight of the HPDC.

The present solid compositions may be produced using any one of many suitable methods, a number of which are conventional and well known in the art. The production method chosen depends, in large measure, on the desired form of the composition. In one particularly useful embodiment, a tableting method, e.g., a conventional tableting method, is employed to produce the present solid compositions in the form of tablets. In tableting a composition according to the invention, conventional tableting additives, such as sugar based excipients, e.g., lactose, surfactants, e.g., sodium lauryl sulphate, polyoxy-ethyleneglycol monoalkyl ethers, alkyl-aryl ethoxylates or saccharide esters, and water soluble polymers, such as polyvinylpyrrolidone and polyethylene glycol, may be employed.

The HPRA, e.g., in the present solid compositions, may be combined with one or more other components. Such other components may include, for example, fillers, binders, tonicity agents, contact lens conditioning/wetting agents, buffering components, lubricating agents and the like. Each of these components may be present, if at all, in an amount effective to perform its designated function or functions. Examples of each of these types of components are conventional and well known in the art. Therefore, a detailed description of such components is not presented here.

In a particularly useful embodiment, the present compositions further include at least one enzyme effective to remove debris from a contact lens. Among the types of debris that form on contact lens during normal use are protein-based debris, mucin-based debris, lipid-based debris and carbohydrate-based debris. One or more types of debris may be present on a single contact lens.

The enzyme employed may be selected from peroxide-active enzymes which are conventionally employed in the enzymatic cleaning of contact lenses. For example, many of the enzymes disclosed in Huth et. al. U.S. Reissue Patent 32,672 and Karageozian et al U.S. Pat. No. 3,910,296 are useful in the present invention. These patents are incorporated in their entirety by reference herein. Among the useful enzymes are those selected from proteolytic enzymes, lipases and mixtures thereof.

Preferred proteolytic enzymes are those which are substantially free of sulfhydryl groups or disulfide bonds, whose presence may react with the active oxygen in the HPLM to the detriment of the activity of the enzyme. Metalloproteases, those enzymes which contain a divalent metal ion such as calcium, magnesium or zinc bound to the protein, may also be used.

A more preferred group of proteolytic enzymes are the serine proteases, particularly those derived from Bacillus and Streptomyces bacteria and Asperigillus molds. Within this grouping, the still more preferred enzymes are the derived alkaline proteases generically called subtilisin enzymes. Reference is made to Deayl, L., Moser, P. W. and Wildi, B. S., "Proteases of the Genus Bacillus. II Alkaline Proteases", Biotechnology and Bioengineering, Vol. XII, pp 213–249 (1970) and Keay, L. and Moser, P. W., "Differentiation of Alkaline Proteases form Bacillus Species" Biochemical and Biophysical Research Comm., Vol 34, No. 5, pp 600–604, (1969).

The subtilisin enzymes are broken down onto two subclasses, subtilisin A and subtilisin B. In the subtilisin A grouping are enzymes derived from such species are *B. subtilis*, *B. licheniformis* and *B. pumilis*. Organisms in this sub-class produce little or no neutral protease or amylase. The subtilisin B sub-class is made up of enzymes from such organisms a *B. subtilis*, *B. subtilis* var. *amylosacchariticus*, *B. amyloliquefaciens* and *B. subtilis* NRRL B3411. These organisms produce neutral proteases and amylases on a level about comparable to their alkaline protease production. One or more enzymes from the subtilisin A sub-class are particularly useful.

In addition other preferred enzymes are, for example, pancreatin, trypsin, collaginase, keratinase, carboxylase, aminopeptidase, elastase, and aspergillo-peptidase A and B, pronase E (from *S. griseus*) and dispase (from *Bacillus polymyxa*).

An effective amount of enzyme is to be used in the practice of this invention. Such amount will be that amount which effects removal in a reasonable time (for example overnight) of substantially all of at least one type of debris from a lens due to normal wear. This standard is stated with reference to contact lens wearers with a history of normal pattern of lens debris accretion, not the very small group who may at one time or another have a significantly increased rate of debris accretion such that cleaning is recommended every day, or every two or three days.

The amount of enzyme required to make an effective cleaner will depend on several factors, including the inherent activity of the enzyme, and the extent of its interaction with the hydrogen peroxide present.

As a basic yardstick, the working solution should contain sufficient enzyme to provide about 0.001 to about 3 Anson units of activity, preferably about 0.01 to about 1 Anson units, per single lens treatment. Higher or lower amounts may be used.

Enzyme activity is pH dependent so for any given enzyme, there is a particular pH range in which that enzyme will function best. The determination of such range can readily be done by known techniques.

The present solid compositions which include such lens cleaning enzymes may be structured to release the enzyme in the liquid medium which contacts the composition at any time relative to the other component or components of the composition provided that the released enzyme is effective at the conditions present in the liquid medium to perform the cleaning function, as described herein. In one particularly useful embodiment, the cleaning enzyme is released in the liquid medium at substantially the same time as the HPRA is so released.

A particularly useful embodiment of the present invention involves a composition comprising solid hydrogen peroxide precursor and HPRA, preferably solid HPRA. The solid hydrogen peroxide precursor is capable of forming hydrogen peroxide after being released in a liquid medium. The HPRA is present in an amount effective after release, e.g., dissolution, in the liquid medium to enhance the antimicrobial activity of the composition/liquid medium combination. Thus, this composition, e.g., in the form of a tablet, pill, capsule, mass of particles and the like, may be combined with, e.g., placed in a liquid medium, as described elsewhere herein, preferably at or about the same time the lens to be disinfected is first contacted with the liquid medium. The HPRA is released, e.g., dissolves, into this medium and hydrogen peroxide begins to be formed from the solid hydrogen peroxide precursor. The lens is effectively disinfected. In one embodiment, such compositions including solid hydrogen peroxide precursor, are substantially free of peroxidase. Thus, acceptable contact lens disinfection is provided using hydrogen peroxide precursor/HPRA-containing compositions which are substantially peroxidase-free.

Preferably, the composition/liquid medium combination has increased antimicrobial activity relative to a reference composition/liquid medium combination containing the same liquid medium, the same concentration of hydrogen peroxide and being substantially free of HPRA. In addition, in one embodiment, the composition further comprises a transition metal ion source, preferably a solid transition metal ion source which forms transition metal ions in the liquid medium in an amount effective to further enhance the antimicrobial activity of the composition/liquid medium combination. Compositions which are substantially free of transition metal component are quite effective in disinfecting contact lenses.

The HPRA and transition metal ion source or precursor useful with the solid hydrogen peroxide precursor are substantially the same as described elsewhere herein and are present in amounts substantially similar to those described elsewhere herein. Also, such solid hydrogen peroxide precursor-containing compositions may be produced using any suitable method, a number of which are conventional and well known in the art.

Among the useful solid hydrogen peroxide precursors are ophthalmically acceptable perborates, percarbonates, percarboxylic acids, salts of percarboxylic acids, urea peroxide, and the like and mixtures thereof. Alkali and alkaline earth metal, in particular sodium and potassium, persalts are preferred if a persalt is to be used as the hydrogen peroxide precursor. The hydrogen peroxide precursor is preferably other than percarbonate, which has been found to provide reduced antimicrobial activity relating to other hydrogen peroxide precursors.

In one embodiment, the solid hydrogen peroxide precursor includes at least one enzyme capable of forming hydrogen peroxide in the liquid medium and at least one host material on which the enzyme acts to form hydrogen peroxide. Any suitable hydrogen peroxide producing enzyme may be employed provided that such enzyme or enzymes have no substantial detrimental effect on the present system, on the lens to be disinfected or on the wearer of the disinfected lens. Among the hydrogen peroxide-producing enzymes useful in the present invention are the following:

Aryl alcohol oxidase
L. Gluconolactone oxidase
Galactose oxidase
Aldehyde oxidase
Glycolate oxidase
Lactate oxidase
Glucose oxidase
Hexose oxidase
Xanthine oxidase
Pyrubate oxidase
Oxalate oxidase
Dihydro-orotate dehydrogenase
L-Amino acid oxidase
D-Amino acid oxidase
Mono Amine oxidase
Pyridoxamine phosphate oxidase
Diamine oxidase histaminase
Sarcosine oxidase
N-methyl-amino acid oxidase
Spermine oxidase
Nitroethane oxidase
Sulphite oxidase and mixtures thereof. The host material or materials to be utilized, of course, depend on the specific hydrogen peroxide-producing enzyme being utilized. Also, such host material should have no substantial detrimental effect on the present system, on the lens being disinfected or on the wearer of the disinfected lens.

One particularly useful hydrogen peroxide producing enzyme is glucose oxidase. When such enzyme is employed, the preferred host material is glucose.

The solid hydrogen peroxide precursor HPRA-containing composition preferably further includes a separation barrier component in an amount effective to separate these two components so that no premature interaction occurs, e.g., during storage. The composition, and in particular, the separation barrier component is structured to release the HPRA in the liquid medium at about the same time the solid hydrogen peroxide precursor is so released. The separation barrier components useful in the present invention are preferably at least partially soluble in the liquid medium to be used, in disinfecting the lens. Materials useful in the barrier components, described elsewhere herein, may also be used in the present separation barrier components. Often, reduced amounts of such materials are employed in the separation barrier component since it is preferred that the hydrogen peroxide precursor and HPRA be released in the liquid medium at about the same time. An alternate approach to reducing premature interaction between the hydrogen peroxide precursor and the HPRA is to store the composition in an atmosphere having reduced or substantially no humidity.

As a safety feature, to reduce the chances of hydrogen peroxide being inadvertently placed in the lens wearer's eye, the HPRA in such solid hydrogen peroxide precursor/ HPRA-containing compositions is preferably present in an amount sufficient to reduce all the hydrogen peroxide which potentially could be formed from the composition's solid hydrogen peroxide precursor. The presence of such amounts of HPRA have little or no detrimental effect on the enhanced antimicrobial activity achieved by the present compositions.

Other components, such as described elsewhere herein, may be included in the present solid hydrogen peroxide precursor/HPRA-containing compositions. For example, the composition may include an effective amount of one or more of the "cleaning" enzymes, e.g., such as those described elsewhere herein. In addition, such compositions may include one or more HPDCs, in particular an HPDC having a chemical make-up other than that of the HPRA being employed, in an amount to destroy all the hydrogen peroxide which potentially could be formed from the solid hydrogen peroxide precursor. When such a HPDC is included, the composition is preferably structured, e.g., in a manner analogous to that described elsewhere herein, to delay the release of the HPDC in the liquid medium until after the hydrogen peroxide precursor and HPRA are released and until after the lens is effectively disinfected. Such solid hydrogen peroxide/HPRA/HPDC-containing compositions are preferably substantially free of peroxidase which is to be released in the liquid medium prior to when the HPDC is so released. The HPDC in such compositions may include a peroxidase and/or a catalase.

One of the advantages of using solid hydrogen peroxide precursors (other than the hydrogen peroxide-producing enzymes and host materials) is that excessive amounts of hydrogen peroxide are not formed in the liquid medium. Thus, the HPRA may act, not only to enhance antimicrobial activity, but also to control, e.g., destroy, excess hydrogen peroxide which may be formed. Thus, the need for an additional HPDC is reduced, if not eliminated.

The solid hydrogen peroxide precursor/solid HPRA-containing compositions may be produced using conventional and well known manufacturing, e.g., tableting techniques.

Using the present compositions to disinfect, and preferably clean, a contact lens may be accomplished by contacting the lens to be disinfected with the composition, if the composition includes a liquid medium, or with a combination of the composition and a liquid medium at conditions effective to effectively disinfect the lens.

In the event that a debris removing enzyme is present in the composition, the contact lens in the liquid medium is also effectively cleaned of such debris. This cleaning action can occur before the lens is disinfected, at the time the lens is being disinfected, or after the lens is disinfected.

It is preferred that the HPDC, if any, not be released into the liquid medium until the lens has been contacted with, e.g., immersed in, liquid medium for a time sufficient, more preferably in the range of about 1 minute to about 4 hours and still more preferably in the range of about 5 minutes to about 1 hour, to effectively disinfect the lens. It is also preferred that substantially all of the residual hydrogen peroxide in the liquid medium be destroyed in less than about 3 hours, more preferably in less than about 1 hour and still more preferably in less than about 30 minutes, after the HPDC, if any, is initially released in the liquid medium.

The disinfecting contacting preferably occurs at a temperature to maintain the liquid medium substantially liquid. It is preferred that the contacting temperature be in the range of about 0° C. to about 100° C., and more preferably in the range of about 10° C. to about 60° C. and still more preferably in the range of about 15° C. to about 30° C. Contacting at or about ambient temperature is very convenient and useful. The contacting preferably occurs for a time to effectively disinfect the lens being treated. Such contacting times can be in the range of about 1 minute to about 12 hours or more.

After such contacting, the liquid medium preferably includes substantially no residual hydrogen peroxide, and the disinfected lens can be removed from this liquid medium and placed directly into the eye for safe and comfortable wear. However, if the liquid medium includes one or more "cleaning" enzymes, it is preferred to rinse the disinfected lens, e.g., with saline, to free the lens of such enzyme prior to placing the disinfected lens into the eye.

The following non-limiting examples illustrate certain aspects of the present invention.

EXAMPLES 1 TO 5

A series of compositions were prepared. Each of the compositions included components as set forth in Table 1. Note that none of the compositions identified in Tables 1 to 9 included any peroxidase. All of these compositions were tested in 10 ml of aqueous liquid medium. Compositions which included no hydrogen peroxide were tested in saline solution.

Each of these compositions was tested as follows. The microorganism *C. albicans* was selected for testing. For each test, such microorganisms were added to 10 ml of a 0.2% (w/v) hydrogen peroxide saline solution, to 10 ml of a 0.5% (w/v) hydrogen peroxide saline solution or to 10 ml of a saline solution with no hydrogen peroxide. The solution was then combined with the given composition to start the test, which was to determine the antimicrobial activity of the composition/solution combination being tested. The D-value, which was determined following the standard procedure, is defined as the length of time required to reduce the microbial burden or load by one log unit.

Results of these tests were as follows:

TABLE 1

| Example | % $H_2O_2$, (w/v) | $CuSO_4$ mg | Ascorbic Acid, mg | pH adjuster used | pH | Extrapolated D-Value, 23° C., min |
|---|---|---|---|---|---|---|
| 1 | 0.2 | 1.0 | 24 | Sodium Borate | 7.0 | 3.6 |
| 2 (Comparative) | 0.2 | 1.0 | — | — | 3.1 | (1) |
| 3 (Comparative) | — | 1.0 | 24 | — | 3.2 | 9.6 |
| 4 | — | 1.0 | — | — | 6.2 | (1) |

TABLE 1-continued

| Example | % $H_2O_2$, (w/v) | $CuSO_4$, mg | Ascorbic Acid, mg | pH adjuster used | pH | Extrapolated D-Value, 23° C., min |
|---|---|---|---|---|---|---|
| (Comparative) 5 (Comparative) | 0.5 | 1.0 | — | Sodium carbonate | not measured | 108 |

(1) No D-value was calculated since there was less than a one log unit reduction in the microbial burden or load in 2 hours.

These results demonstrate that the combination of $H_2O_2$/$CuSO_4$/ascorbic acid (Composition 1), in accordance with the present invention, has outstanding antimicrobial activity relative to combinations containing $H_2O_2$/ $CuSO_4$ (Compositions 2 and 5), $CuSO_4$/ascorbic acid (Composition 3), and $CuSO_4$ (composition 4).

EXAMPLES 6 TO 14

A series of compositions were prepared. Each of the compositions included the components as set forth in Table 2.

Each of these compositions was tested as follows. Microorganisms, C. albicans, were combined with 10 ml of a saline solution containing hydrogen peroxide, as indicated below, and this contaminated liquid was added to the composition. In Examples 12, 13 and 14, varying concentrations of hydrogen peroxide were used with no other composition except the indicated pH adjuster. The D-value for each of these compositions was then determined, as described in Examples 1 to 5.

Results of these tests were as follows:

transition metal ions, such as $Cu^{+2}$ ions, (Compositions 6, 7, 8 and 11) have enhanced antimicrobial activity relative to compositions which contain the same amount (Compositions 12 and 13) or even more (Composition 14) of hydrogen peroxide. Even at very low concentrations of ascorbic acid and transition metal ions (Compositions 9 and 10) some enhancement in antimicrobial activity is apparent relative to compositions containing the same concentration of $H_2O_2$ (Compositions 12 and 13).

EXAMPLES 15 TO 19

A series of compositions were prepared. Each of the compositions included the components as set forth in Table 3.

Each of these compositions was tested as follows. Various microorganisms, as indicated in Table 3 below, were combined with 10 ml of saline solution containing 0.5% (w/v) of hydrogen peroxide or with 10 ml of saline solution containing no hydrogen peroxide, as indicated below. D-values on the various microorganisms for each of these compositions were then determined, as described in Examples 1 to 5.

Results of these tests were as follows:

TABLE 2

| Example | % $H_2O_2$, (w/v) | $CuSO_4$, mg | Ascorbic Acid, mg | pH adjuster used | pH | Extrapolated D-Value, 23° C., min |
|---|---|---|---|---|---|---|
| 6 | 0.5 | 1.0 | 24 | Sodium Carbonate | 7.1 | 2.6 |
| 7 | 0.5 | 0.2 | 2.4 | Sodium Carbonate | 6.5 | 3.8 |
| 8 | 0.5 | 1.0 | 1.0 | Sodium Carbonate | 4.7 | 3.1 |
| 9 | 0.5 | 0.01 | 0.24 | Sodium Carbonate | not measured | 45.6 |
| 10 | 0.5 | 0.1 | 0.1 | Sodium Carbonate | not measured | 28.2 |
| 11 | 0.1 | 1.0 | 24 | Sodium Borate | 7.4 | 5.2 |
| 12 (Comparative) | 0.5 | — | — | Sodium Carbonate | 7.0 | 30 |
| 13 (Comparative) | 0.5 | — | — | Sodium Carbonate | 7.3 | 60 |
| 14 (Comparative) | 3.0 | — | — | Sodium Carbonate | 7.0 | 7.2 |

These results demonstrate that compositions which include $H_2O_2$, and sufficient amounts of ascorbic acid and

TABLE 3

| Example | % $H_2O_2$, (w/v) | $MnSO_4$, mg | Ascorbic Acid, mg | pH adjuster used | pH | Extrapolated D-Value, 23° C., min[1] |
|---|---|---|---|---|---|---|
| 15 | 0.5 | 1.0 | 10 | Sodium borate | 7.8 | 2.6, 2.5, 87.0, 17.6 |
| 16 | 0.5 | 1.0 | — | Sodium borate | 7.8 | 15.5, 15.0, 98.0, 69.6 |
| 17 | 0.5 | — | 10 | Sodium borate | 7.8 | 5.2, 2.5, 94.0, 34.8 |
| 18 (Comparative) | — | 1.0 | 10 | Sodium borate | 7.8 | 172, 420, 797,[2] |
| 19 (Comparative) | 0.5 | — | — | Sodium borate | 7.8 | 39.0, 321 80.0, 84.4 |

[1]D-values were on *S. Aureus, S. Marcescens, A. Niger,* and *C. Albicins,* respectively.
[2]No D-value was calculated since there was less than a one log unit reduction in the microbial burden or load in 2 hours.

These results indicate that the combination of hydrogen peroxide/ascorbic acid (Composition 17) and the combination of hydrogen peroxide/$Mn^{+2}$/ ascorbic acid (Composition 15) provide enhanced antimicrobial activity relative to compositions which include no hydrogen peroxide (Composition 18) or no ascorbic acid (Composition 16 and 19).

EXAMPLES 20 TO 35

A series of compositions were prepared. Each of the compositions included the components as set forth in Table 4.

Each of these compositions was tested as follows. Microorganisms, *C. albicans,* were combined with 10 ml of a saline solution containing hydrogen peroxide, as indicated below, and this contaminated liquid was added to the composition. In Examples 30 to 35, varying concentrations of hydrogen peroxide were used with no other composition except the indicated pH adjuster. The D-value for each of these compositions was then determined, as described in Examples 1 to 5.

Results of these tests were as follows.

TABLE 4

| Examples | % $H_2O_2$, (w/v) | $MnSO_4$, mg | Ascorbic Acid, mg | pH adjuster used | pH | Extrapolated D-Value, 23° C., min |
|---|---|---|---|---|---|---|
| 20 | 0.5 | 1.0 | 10 | Sodium Carbonate | 7.1 | 2.6 |
| 21 | 0.5 | 0.1 | 1.0 | Sodium Carbonate | not measured | 35.4 |
| 22 | 0.5 | 0.3 | 3.0 | Sodium borate | 7.4 | 26.7 |
| 23 | 0.5 | 0.3 | 3.0 | Sodium borate | 8.0 | 13.0 |
| 24 | 0.5 | 0.3 | 3.0 | Sodium borate | 8.6 | 41.9 |
| 25 | 0.5 | 0.1 | 1.0 | Sodium borate | 7.4 | 28.0 |
| 26 | 0.5 | 0.3 | 6.0 | Sodium borate | 7.4 | 45.7 |
| 27 | 0.5 | 0.3 | 6.0 | Sodium borate | 7.4 | 19.8 |
| 28 | 0.5 | 0.3 | 1.0 | Sodium borate | 7.4 | 46.3 |
| 29 | 0.5 | 0.3 | 3.0 | Sodium borate | 7.4 | 50.7 |
| 30 (Comparative) | 3.0 | — | — | Sodium carbonate | 7.0 | 7.2 |
| 31 (Comparative) | 3.0 | — | — | Sodium borate | 7.4 | 16.7 |
| 32 (Comparative) | 3.0 | — | — | Sodium borate | 7.4 | 10.6 |
| 33 (Comparative) | 0.5 | — | — | Sodium carbonate | 7.0 | 30 |
| 34 (Comparative) | 0.5 | — | — | Sodium carbonate | 7.3 | 60 |
| 35 (Comparative) | 0.5 | — | — | Sodium borate | 7.4 | 60 |

These results indicate that the combination of hydrogen peroxide/ascorbic acid/$Mn^{+2}$ (Compositions 20 to 29) provide enhanced antimicrobial activity relative to compositions containing the same concentration of hydrogen peroxide with no ascorbic acid and $Mn^{+2}$ at comparable pH (Compositions 33, 34 and 35). In certain instances (Compositions 20 and 23), such combinations provide enhanced antimicrobial activity relative to compositions which contain higher concentrations of hydrogen peroxide (Compositions 30, 31 and 32). The pH of the combination may also affect antimicrobial activity. Increased, or even optimal, antimicrobial activity can be achieved by controlling the concentration of the HPRA and other activator or activators and the pH the combination.

EXAMPLES 36 TO 39

A series of compositions were prepared. Each of the compositions included the components as set forth in Table 5.

Each of these compositions was tested in accordance with the procedures outlined in Examples 6 to 14.

Results of these tests were as follows:

TABLE 5

| Examples | % $H_2O_2$, (w/v) | FeEDTA mg | Ascorbic Acid, mg | pH adjuster used | pH | Extrapolated D-Value, 23° C., min |
|---|---|---|---|---|---|---|
| 36 | 0.1 | 1.0 | 24 | Sodium borate | 7.4 | (1) |
| 37 | 0.1 | 1.0 | 1.0 | Sodium borate | 7.4 | 66 |
| 38 (Comparative) | — | 1.0 | 24 | Sodium borate | 7.4 | (1) |
| 39 (Comparative) | 0.1 | 1.0 | — | Sodium borate | 6.3 | 78 |

(1) No D-value was calculated since there was less than a one log unit reduction in the microbial burden or load in 2 hours.

Composition 36 showed low antimicrobial activity. However, when the concentration of ascorbic acid was reduced (Composition 37) relative to Composition 36, enhanced antimicrobial activity is achieved with a system which included Fe EDTA.

EXAMPLES 40 TO 56

A series of solid compositions were prepared. Each of the compositions included the components as set forth in Table 6. Each of these compositions was tested in accordance with the procedure outlined in Examples 6 to 14.

Results of these tests are as follows:

TABLE 6

| Examples | Perborate, (mg) | Metal, mg | Ascorbic Acid, mg | pH adjuster used | pH | Extrapolated D-Value, 23° C., min[(1)] |
|---|---|---|---|---|---|---|
| 40 | 10 | $CuSO_4$ 0.1 | 2.4 | — | not measured | —, —, — 13.4 |
| 41 | 10 | $MnSO_4$ 0.3 | 3.0 | Sodium borate | 7.5 | —, —, — 14.0 |
| 42 (Comparative) | — | $CuSO_4$ 0.1 | 2.4 | Sodium carbonate | not measured | —, —, — 16.5 |
| 43 (Comparative) | — | $MnSO_4$ 0.3 | 3.0 | Sodium borate | 8.0 | —, —, — 588 |
| 44 | 10 | $MnSO_4$ 0.3 | 3.0 | Sodium borate | 8.0 | —, —, — 33.0 |
| 45 | 5.0 | $MnSO_4$ 0.3 | 3.0 | Sodium borate | 8.0 | —, —, — 27.0 |
| 46 | 2.0 | $MnSO_4$ 0.3 | 3.0 | Sodium borate | 8.0 | —, —, — 63.0 |
| 47 | 10.0 | $MnSO_4$ 0.3 | 3.0 | Sodium borate | 7.5 | 3.0, 3.0, —, 67.0 |
| 48 | 10.0 | — | 3.0 | Sodium borate | 7.5 | 8.0, 5.0, —, 41.0 |

TABLE 6-continued

| Examples | Perborate, (mg) | Metal, mg | Ascorbic Acid, mg | pH adjuster used | pH | Extrapolated D-Value, 23° C., min[1] |
|---|---|---|---|---|---|---|
| 49 | 10.0 | MnSO$_4$ 0.3 | 6.0 | Sodium borate | 7.5 | 5.0, 5.0, —, 74.0 |
| 50 | 10.0 | — | 6.0 | Sodium borate | 7.5 | 5.0, 5.0, —, 41.0 |
| 51 | 10.0 | — | 1.5 | Sodium borate | 7.5 | 5.0, 5.0, —, 68.0 |
| 52 | 10.0 | MnSO$_4$ 1.0 | 5.0 | Sodium borate | 7.5 | 8.0, 10.0, (2), 96.0 |
| 53 | 5.0 | MnSO$_4$ 1.0 | 2.5 | Sodium borate | 7.5 | 8.0, 11.0, (2), 80.0 |
| 54 | 2.0 | MnSO$_4$ 1.0 | 1.0 | Sodium borate | 7.5 | 32.0, 28.0 (2), 91.0 |
| 55 | 10.0 | — | 5.0 | Sodium borate | 7.5 | 8.0, 7.0, (2), 77.0 |
| 56 | 10.0 | — | — | Sodium borate | 7.5 | 8.0, 32.0, (2), (2) |

(1) D-Values were on S. Aureus, S. Marcenscens, A. Niger, and C. Albicans respectively.

(2) No D-value was calculated since there was less than a one log unit reduction in the microbial burden or load in 2 hours.

Comparing Compositions 40 and 41 to 42 and 43, respectively, the antimicrobial activity of the combination of perborate/metal/ascorbic acid is enhanced relative to the combination of metal/ascorbic acid without perborate. The value of the transition metal component may depend on the microorganism involved. See, for example, Compositions 47 and 48, Compositions 49 and 50, and Compositions 52 and 55. Comparing Compositions 44, 45 and 46, the antimicrobial activity is dependent to some extent on the ratio of perborate to activators. Care should be taken to avoid use of excessive amounts of activators, in particular HPRA. In certain instances, a composition which is substantially free of transition metal component provides enhanced antimicrobial activity. See Compositions 49 and 50.

EXAMPLES 57 AND 58

A series of two (2) compositions were prepared. Each of these compositions included the components as set forth in Table 7, and further included 10 mg of glucose oxidase and 200 mg of glucose in 10 ml of saline solution.

Each of these compositions was tested, on the microorganisms noted below, in accordance with the procedure outlined in Examples 6 to 14.

Results of these tests were as follows:

TABLE 7

| Examples | Metal, mg | Ascorbic Acid, mg | pH adjuster used | pH | Extrapolated D-Value, 23° C., min[1] |
|---|---|---|---|---|---|
| 57 | FeEDTA 1.0 | 24 | Sodium borate | 7.4 | (2), 45.0 |
| 58 | CuSO$_4$ 1.0 | 24 | Sodium borate | 7.4 | 5.7, 10.1 |

(1) D-Values were on S. Marcenscens and S. Epidermidis respectively.
(2) No D-value was calculated since there was less than a one log unit reduction in the microbial burden or load in 2 hours.

These results indicate that enzymatically derived hydrogen peroxide is effective in combination with transition metal and ascorbic acid as a contact lens disinfectant.

EXAMPLES 59 TO 62

A series of compositions were prepared utilizing glutathione. Each of the compositions included the components set forth in Table 8.

Each of these compositions were tested in accordance with the procedure outlined in Examples 6 to 14.

Results of these tests were as follows:

TABLE 8

| Examples | % H$_2$O$_2$ (w/v) | CuSO$_4$, mg | Glutathione, mg | pH adjuster used | pH | Extrapolated D-Value, 23° C., min |
|---|---|---|---|---|---|---|
| 59 | 0.2 | 1.0 | 40 | Sodium borate | 7.5 | (1) |
| 60 | 0.5 | 1.0 | 5.0 | Sodium carbonate | not measured | 53 |
| 61 | 0.5 | 1.0 | 5.0 | Sodium carbonate | not measured | 42 |
| 62 | 0.5 | 1.0 | 1.0 | Sodium carbonate | not measured | 19.8 |

(1) No D-value was calculated since there was less than a one log unit reduction in the microbial burden or load in 2 hours.

These results indicate that glutathione is effective to enhance antimicrobial activity of hydrogen peroxide. Care should be exercised to avoid excessive amounts of glutathione.

EXAMPLES 63 TO 66

A series of compositions were prepared using either sodium perborate or sodium percarbonate as a hydrogen peroxide precursor. Each of the compositions included the components set forth in Table 9.

Each of these compositions was tested in accordance with the procedure outlined in Examples 6 to 14.

TABLE 9

| Examples | Precursor, mg | MnSO$_4$, mg | Ascorbic Acid, mg | pH adjuster used | pH | Extrapolated D-Value, 23° C., min |
|---|---|---|---|---|---|---|
| 63 | Perborate 10 | 0.3 | 3.0 | Sodium borate | 8.0 | 33.0 |
| 64 | Perborate | 0.3 | 3.0 | Sodium | 8.0 | 27.0 |

TABLE 9-continued

| Examples | Precursor, mg | MnSO$_4$, mg | Ascorbic Acid, mg | pH adjuster used | pH | Extrapolated D-Value, 23° C., min |
|---|---|---|---|---|---|---|
| 65 | 5.0 Perborate | 0.3 | 3.0 | borate Sodium borate | 8.0 | 63.0 |
| 66 | 2.0 Percarbonate 10 | 0.3 | 3.0 | Sodium borate | 8.0 | 47.0 |

These results indicate that perborate provides increased antimicrobial activity in the present system relative to percarbonate.

EXAMPLES 67

This example illustrates a lens cleaning/disinfecting embodiment of the present invention.

A protein-based debris laden contact lens is placed in a plastic container. 10 ml of a saline solution containing 0.1% (w/v) of $H_2O_2$ and 0.3% by weight of boric acid is added to the container. The pH of this solution is about 7.5.

A layered, delayed release tablet is dropped into the solution in the container. The center core of this tablet includes 1.5 mg of crystalline catalase. The outer layer of the tablet includes 1 mg of $CuSO_4$, 3 mg of ascorbic acid and 0.4 mg of subtilisin A enzyme. A delayed release layer between the inner layer and the outer layer is structured and designed to dissolve sufficiently in two hours after being exposed to the solution in the container to release the catalase in the solution.

Upon being dropped into the solution, the outer layer of the tablet dissolves to release the $CuSO_4$, ascorbic acid and subtilisin A into the solution. The enzyme in the outer layer begins to attack and remove the protein-based debris on the lens. Substantially all of the protein-based debris is removed from the lens. In addition, the contact lens is effectively disinfected. Two hours after the layered tablet is first dropped into the solution, the catalase is released in the solution and destroys the residual hydrogen peroxide in the solution. Three hours after the contact lens is first introduced into the solution, it is removed from the solution, rinsed with physiological saline solution to remove the subtilisin A enzyme and placed in the wearer's eye. It is found that after three hours, the contact lens is effectively disinfected and cleaned of protein-based debris. The lens wearer experiences no discomfort or eye irritation from wearing the disinfected and cleaned contact lens.

EXAMPLE 68

Example 67 is repeated except that the saline solution contains 0.5% (w/v) of $H_2O_2$, and the outer layer of the tablet contains no $CuSO_4$.

Three hours after the contact lens is first introduced into the solution it is removed from the solution, rinsed with physiological saline solution to remove the subtilisin A enzyme and placed in the wearer's eye. It is found that after three hours, the contact lens is effectively disinfected and cleaned of protein-based debris. The lens wearer experiences no discomfort or eye irritation from wearing the disinfected and cleaned contact lens.

EXAMPLE 69

Example 67 is repeated except that the saline solution contains no hydrogen peroxide, and the outer layer of the tablet contains 200 mg of glucose and 10 mg of glucose oxidase.

Three hours after the contact lens is first introduced into the solution it is removed from the solution, rinsed with physiological saline solution to remove the subtilisin A enzyme and placed in the wearer's eye. It is found that after three hours, the contact lens is effectively disinfected and cleaned of protein-based debris. The lens wearer experiences no discomfort or eye irritation from wearing the disinfected and cleaned contact lens.

EXAMPLE 70

Example 67 is repeated except that the saline solution contains no hydrogen peroxide, and a differently formulated tablet is used. The tablet used contains 10 mg of sodium perborate, 1 mg of $CuSO_4$, 20 mg of ascorbic acid and 0.4 mg of subtilisin A enzyme. The amount of ascorbic acid is sufficient to reduce all the hydrogen peroxide that potentially could be formed from the sodium perborate. The tablet also includes a barrier designed to separate the perborate from the $CuSO_4$ and ascorbic acid during storage. This barrier is structured to dissolve promptly upon introducing the tablet into the saline solution. No additional hydrogen peroxide destroying component, e.g., catalase, is included.

Three hours after the contact lens is first introduced into the solution it is removed from the solution, rinsed with physiological saline solution to remove the subtilisin A enzyme and placed in the wearer's eye. It is found that after three hours, the contact lens is effectively disinfected and cleaned of protein-based debris. The lens wearer experiences no discomfort or eye irritation from wearing the disinfected and cleaned contact lens.

EXAMPLE 71

A series of layered, delayed release tablets were prepared. Each of the layered tablets had a core or inner tablet which included catalase, buffers and other conventional components. Further, this core tablet was surrounded by a material which delayed the release of the contents of the core tablet into the hydrogen peroxide-containing liquid medium, described below, for more than 2 hours after the layered tablet is first introduced into the hydrogen peroxide-containing liquid medium. For all layered tablets tested, the composition of the core tablet and the delayed release layer was substantially the same.

Layered tablets were tested. Each of these tablets had an outer layer which had the following composition:

|  | OUTER LAYER, mg |
|---|---|
| Triethyl citrate | 0.65 |
| Polyvinylpyrrolidone | 10.75 |
| Ascorbic acid | 5.46 |
| Manganese sulfate | 1.09 |

20 of these layered tablets were selected for testing. Each of 10 of the layered tablets was introduced into 10 ml of a 0.5% (w/v) hydrogen peroxide solution in deionized water. Each of the other 10 of the layered tablets was introduced into 10 ml of a 0.45% (w/v) saline solution containing 0.5% (w/v) hydrogen peroxide solution in deionized water. A predetermined amount of C. albicans microorganisms was also introduced into each solution. The log reduction in microbial burden at 2 hours, after the introduction of the layered tablet into the liquid medium, was determined.

The mean log reduction value of each of these groups of layered tablets was as follows:

| | Mean Log Reduction In Microbial Burden |
|---|---|
| Outer Layer B Deionized Water | 1.37 |
| Outer Layer B Saline | 2.49 |

These results indicate that the presence of chloride ion during the disinfecting process has a beneficial effect on antimicrobial activity.

EXAMPLE 72

A layered tablet having the following composition was prepared.

| Core Tablet | |
|---|---|
| Sodium perborate | 10 mg |
| Sodium carbonate | 15 mg |
| Polyethylene glycol | 2 mg |
| Sodium chloride | 10 mg |
| Coating | |
| Mixture of tartaric acid, ascorbic acid and polyvinylpyrrolidone | 18 mg |

This layered tablet was dissolved in 10 ml of a 0.45% (w/v) aqueous saline solution. 1 mg of $CoCl_2.6H_2O$ was then added to the solution. Immediately, the solution became green in color. Upon complete consumption of the hydrogen peroxide, the solution changed to a pink color. This pink color was the same as that observed after placing 1 mg of $CoCl_2.6H2O$ in the saline solution without the layered tablet.

These results indicate that cobalt ions can be used to indicate the presence, or absence, of hydrogen peroxide. The green color, believed to be due to the presence of $Co^{+3}$, indicates that hydrogen peroxide is present. The pink color, believed to be due to the presence of $Co^{+2}$ indicates that hydrogen peroxide is not present, e.g.,.has been consumed or destroyed.

EXAMPLE 73

Example 72 was repeated except that only a few ppm of $CoCl_2.6H_2O$ was added to the saline solution instead of the 1 mg added in Example 72.

Immediately upon adding the layered tablet, fizzing was observed, and the layered tablet dissolved completely within 20 minutes to produce a greenish colored solution which slowly changed color to lightly pinkish. Thus, even at very low concentrations, the cobalt ion gave an indication of the presence and absence of hydrogen peroxide.

While this invention has been described with respect to various specific examples and embodiments, it is to be understood that the invention is not limited thereto and that it can be variously practiced within the scope of the following claims.

What is claimed is:

1. A composition comprising: solid hydrogen peroxide precursor capable of forming hydrogen peroxide after being released in a liquid medium; a hydrogen peroxide reducing agent in an amount effective for a period of time after being released in the liquid medium to enhance the antimicrobial activity of the composition/liquid medium combination relative to an identical combination without the hydrogen peroxide reducing agent, said period of time being sufficient so that a contact lens in the composition/liquid medium combination is disinfected, said amount of said hydrogen peroxide reducing agent being less than that an amount effective to reduce all the hydrogen peroxide formed in the composition/liquid medium combination, said composition being structured to release said hydrogen peroxide reducing agent in the liquid medium at about the same time said solid hydrogen peroxide precursor is so released; and a hydrogen peroxide destroying component in an amount effective after being released in the liquid medium to destroy all the hydrogen peroxide formed from said solid hydrogen peroxide precursor, said composition being structured to release said solid hydrogen peroxide precursor and said hydrogen peroxide reducing agent in the liquid medium said period of time before said hydrogen peroxide destroying component is so released, and said composition being free of peroxidase which is to be released in the liquid medium prior to when said hydrogen peroxide destroying component is so released.

2. The composition of claim 1 which further comprises a transition metal ion source which after being released in the liquid medium forms transition metal ions in the liquid medium in an amount effective for a period of time to further enhance the antimicrobial activity of the composition/liquid medium combination.

3. The composition of claim 1 wherein said hydrogen peroxide reducing agent is selected from the group consisting of ene-diol compounds and mixtures thereof.

4. The composition of claim 1 which further comprises at least one enzyme which after being released in the liquid medium is capable of removing debris from a contact lens in the liquid medium, said enzyme being present in an amount effective to substantially remove at least one type of debris from a debris laden contact lens contacted with the composition/liquid medium combination.

5. A composition comprising: solid hydrogen peroxide precursor, other than percarbonate, capable of forming hydrogen peroxide after being released in a liquid medium; a hydrogen peroxide reducing agent in an amount effective for a period of time after being released in the liquid medium to enhance the antimicrobial activity of the composition/liquid medium combination relative to an identical combination without the hydrogen peroxide reducing agent, said period of time being sufficient so that a contact lens in the composition/liquid medium combination is disinfected, said amount of said hydrogen peroxide reducing agent being less than that amount effective to reduce all the hydrogen peroxide formed in the composition/liquid medium combination; and a hydrogen peroxide destroying component in an amount effective after being released in the liquid medium to destroy all the hydrogen peroxide formed from said solid hydrogen peroxide precursor, said composition being structured to release said solid hydrogen peroxide precursor and said hydrogen peroxide reducing agent in the liquid medium said period of time before said hydrogen peroxide destroying component is so released, said composition being free of peroxidase, said composition providing enhanced antimicrobial activity after being released in the liquid medium relative to a substantially identical composition including percarbonate as the solid hydrogen peroxide precursor, said enhanced antimicrobial activity being sufficient to disinfect a contact lens in the composition/liquid medium combination.

6. The composition of claim 5 which further comprises a transition metal ion source which after being released in the liquid medium forms transition metal ions in the liquid medium in an amount effective for a period of time to further enhance the antimicrobial activity of the composition/liquid medium combination.

7. The composition of claim 5 wherein said solid hydrogen peroxide precursor is selected from the group consisting of perborates and mixtures thereof, and said hydrogen peroxide reducing agent is selected from the group consisting of ascorbic acid, salts of ascorbic acid and mixtures thereof.

8. A composition comprising: a hydrogen peroxide reducing agent in an amount effective to enhance antimicrobial activity for a period of time after being released in hydrogen peroxide-containing liquid medium relative to an identical hydrogen peroxide-containing medium without the hydrogen peroxide reducing agent, said amount of said hydrogen peroxide reducing agent being less than an amount effective to reduce all the hydrogen peroxide present in the hydrogen peroxide-containing liquid medium; and a hydrogen peroxide destroying component in an amount effective to destroy all the hydrogen peroxide in the hydrogen peroxide-containing liquid medium after being released in the hydrogen peroxide-containing liquid medium, said composition being structured to release said hydrogen peroxide reducing agent in the hydrogen peroxide-containing liquid medium said period of time before said hydrogen peroxide destroying component is so released so that a contact lens in the hydrogen peroxide-containing liquid medium including the released hydrogen peroxide reducing agent is disinfected during said period of time.

9. The composition of claim 8 wherein said hydrogen peroxide reducing agent is other than said hydrogen peroxide destroying component and is selected from the group consisting of ene-diol compounds and mixtures thereof, and said composition is solid.

10. The composition of claim 8 which further comprises at least one enzyme which after being released in a liquid medium is capable of removing debris from a contact lens in the liquid medium, said enzyme being present in an amount effective to substantially remove at least one type of debris from a debris laden contact lens contacted with the hydrogen peroxide-containing liquid medium.

11. The composition of claim 8 which further comprises a transition metal ion source which after being released in the hydrogen peroxide-containing liquid medium forms transition metal ions in the hydrogen peroxide- containing liquid medium in an amount effective for a period of time to further enhance the antimicrobial activity of the composition/hydrogen peroxide-containing liquid medium combination, said composition being structured to release said transition metal ion source in the hydrogen peroxide-containing liquid medium before said hydrogen peroxide destroying component is so released.

12. The composition of claim 1 wherein said solid hydrogen peroxide precursor and said hydrogen peroxide reducing agent after being released in the liquid medium provide the liquid medium with sufficient antimicrobial activity to disinfect a contact lens in the liquid medium prior to the release in the liquid medium of said effective amount of said hydrogen peroxide destroying component.

13. The composition of claim 1 wherein said hydrogen peroxide reducing agent is other than said hydrogen peroxide destroying component.

14. The composition of claim 13 wherein said hydrogen peroxide reducing agent is selected from the group consisting of ene-diol compounds and mixtures thereof.

15. The composition of claim 1 wherein said hydrogen peroxide destroying component includes catalase.

16. The composition of claim 5 wherein said hydrogen peroxide reducing component is other than said hydrogen peroxide destroying component.

17. The composition of claim 16 wherein said hydrogen peroxide reducing agent is selected from the group consisting of ene-diol compounds and mixtures thereof.

* * * * *